United States Patent
Geng et al.

(10) Patent No.: US 11,406,651 B2
(45) Date of Patent: *Aug. 9, 2022

(54) USE OF MANNURONIC DIACID COMPOSITION IN TREATMENT OF VASCULAR DEMENTIA

(71) Applicants: GREEN VALLEY (SHANGHAI) PHARMACEUTICALS CO., LTD., Shanghai (CN); SHANGHAI INSTITUTE OF MATERIA MEDICA, CHINESE ACADEMY OF SCIENCES, Shanghai (CN)

(72) Inventors: Meiyu Geng, Shanghai (CN); Xianliang Xin, Shanghai (CN); Xiaoguang Du, Shanghai (CN); Zhenqing Zhang, Shanghai (CN); Jian Ding, Shanghai (CN)

(73) Assignees: GREEN VALLEY (SHANGHAI) PHARMACEUTICALS CO., LTD., Shanghai (CN); SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/256,738

(22) PCT Filed: Jun. 28, 2019

(86) PCT No.: PCT/CN2019/093813
§ 371 (c)(1),
(2) Date: Dec. 29, 2020

(87) PCT Pub. No.: WO2020/001643
PCT Pub. Date: Jan. 2, 2020

(65) Prior Publication Data
US 2021/0268006 A1 Sep. 2, 2021

(30) Foreign Application Priority Data
Jun. 29, 2018 (CN) .......................... 201810711863.8

(51) Int. Cl.
*A61K 31/702* (2006.01)
*A61P 25/28* (2006.01)

(52) U.S. Cl.
CPC ............ *A61K 31/702* (2013.01); *A61P 25/28* (2018.01)

(58) Field of Classification Search
None
See application file for complete search history.

(56) References Cited

U.S. PATENT DOCUMENTS 8,835,403 B2 * 9/2014 Geng ........................ A61P 5/50
514/53

FOREIGN PATENT DOCUMENTS

CN 106344592 A 1/2017
CN 106344593 A 1/2017

OTHER PUBLICATIONS

Yang, Z., Li, J. P., & Guan, H. S. (2004). Preparation and characterization of oligomannuronates from alginate degraded by hydrogen peroxide. Carbohydrate polymers, 58(2), 115-121. (Year: 2004).*
Jiang, R. W., Du, X. G., Zhang, X., Wang, X., Hu, D. Y., Meng, T., . . . & Shen, J. K. (2013). Synthesis and bioassay of β-(1, 4)-D-mannans as potential agents against Alzheimer's disease. Acta Pharmacologica Sinica, 34(12), 1585-1591. (Year: 2013).*
Athari Nik Azm, S., Vafa, M., Sharifzadeh, M., Safa, M., Barati, A., & Mirshafiey, A. (2017). Effects of M2000 (D-mannuronic acid) on learning, memory retrieval, and associated determinants in a rat model of Alzheimer's disease. American Journal of Alzheimer's Disease & Other Dementias®, 32(1), 12-21. (Year: 2017).*
Lewis, H., Beher, D., Cookson, N., Oakley, A., Piggott, M., Morris, C. M., . . . & Kalaria, R. N. (2006). Quantification of Alzheimer pathology in ageing and dementia: age-related accumulation of amyloid-β (42) peptide in vascular dementia. Neuropathology and applied neurobiology, 32(2), 103-118. (Year: 2006).*
Skillbäck, T., Farahmand, B. Y., Rosen, C., Mattsson, N., Nägga, K., Kilander, L., . . . & Zetterberg, H. (2015). Cerebrospinal fluid tau and amyloid-β1-42 in patients with dementia. Brain, 138(9), 2716-2731. (Year: 2015).*
International Search Report and Written Opinion for Application No. PCT/CN2019/093813, dated Sep. 30, 2019, 15 pages.

* cited by examiner

*Primary Examiner* — Dale R Miller
(74) *Attorney, Agent, or Firm* — McCarter & English, LLP; Wei Song; Sudheer Chava

(57) ABSTRACT

The present invention relates to the application of mannuronic diacid oligosaccharide composition in the treatment of vascular dementia.

18 Claims, 6 Drawing Sheets

USE OF MANNURONIC DIACID COMPOSITION IN TREATMENT OF VASCULAR DEMENTIA

CROSS-REFERENCE TO RELATED APPLICATIONS

This application is a U.S. national stage filing, under 35 U.S.C. § 371(c), of International Application No. PCT/CN2019/093813, filed on Jun. 28, 2019, which claims priority to Chinese Patent Application No. 201810711863.8, filed on Jun. 29, 2018.

TECHNICAL FIELD

The present invention relates to the use of an optimal composition of mannuronic diacids obtained by a biological activity evaluation method in the treatment of vascular dementia.

BACKGROUND OF THE INVENTION

Vascular dementia (VD) refers to severe cognitive dysfunction syndrome caused by cerebrovascular disease. The prevalence of VD in China is 1.1%-3.0%, and the annual incidence is 5-9/1000 people. Its clinical practice is mainly to treat primary cerebrovascular diseases and to prevent the occurrence of VD. For VD patients, vitamin E, vitamin C and *Ginkgo biloba* preparations are used for supportive treatments. There is no ideal therapeutic drug up to now.

Mannuronic diacids have been paid extensive attention due to their potential medicinal values. Mannuronic diacids are usually prepared by multiple steps with alginic acid as a raw material.

The polysaccharide molecule of the raw material, alginic acid, comprises an M segment formed of D-mannuronic acids linked by β-1,4-glucosidic bonds, a G segment formed of L-guluronic acids linked by α-1,4-glucosidic bonds, and an MG segment formed by hybridization of the two saccharides. The structural formulae of D-mannuronic acid and L-guluronic acid are shown in the following Formula (I):

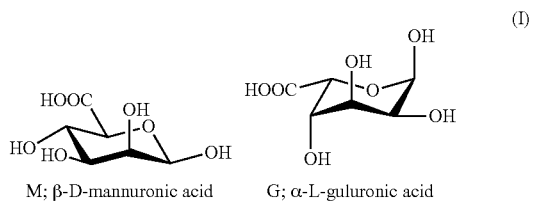

M; β-D-mannuronic acid   G; α-L-guluronic acid

The M segment and the G segment can be separated from the raw material, alginic acids. A common method can be simply described below: alginic acid is preliminarily degraded to give mixed polysaccharides of polymannuronic acid and polyguluronic acid; then the mixed polysaccharides are subjected to acidic precipitation to remove the polyguluronic acid therein, and further refinement is conducted to obtain a homopolymannuronic acid with a purity of more than 90% (hereinafter also referred to as "M-segment intermediate"). See, e.g., the methods disclosed in Chinese Patent Application No. 98806637.8 and CN02823707.2.

A common preparation method of oligomeric mannuronic acid is as follows: the M-segment intermediate obtained above is subjected to further acidolysis by heating under an acidic condition to obtain a small fragment mannuronic acid polymer having a desired molecular weight range. In addition, the degradation efficiency can be improved by an oxidative degradation method; is meanwhile, the reducing end can be oxidized to a ring-opened saccharic diacid, see Chinese Patent Application No. 200580009396.5 (Patent literature 1) filed by Meiyu Geng, et al. and U.S. Pat. No. 8,835,403 B2 (Patent literature 2) for details. For convenience of description, Patent literatures 1 and 2 are hereinafter collectively referred to as prior documents, of which are incorporated herein by reference in their entirety.

The reaction to obtain mannuronic diacid disclosed in prior documents can be represented by the following reaction equation (II), that is, the aldehyde group at position C1 of mannuronic acid at the reducing end of oligomannuronic acid polysaccharide is oxidized to carboxyl group.

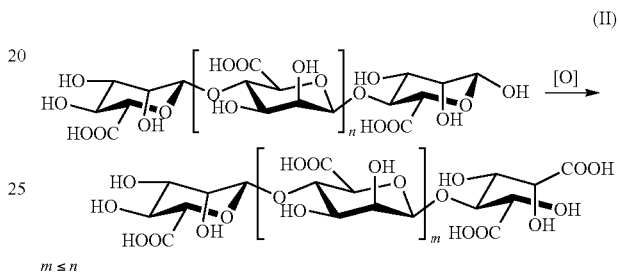

$m \leq n$

In the above oxidative conversion process, a commonly used oxidant is an alkaline copper sulfate solution, i.e. Fehling's reagent. Prior documents just adopt this oxidation method. Specifically, under an alkaline condition, the reaction substrate polymannuronic acid, i.e. the above M-segment intermediate, is added to a copper sulfate solution and reacted in a boiling water bath for 15 minutes to 2 hours. This method uses $Cu^{2+}$ ion as an oxidant to oxidize the aldehyde group, and a brick-red cuprous oxide precipitate is generated in the reaction. This reaction is often used to identify a reducing sugar.

Prior documents disclose that oligomannaric acids have effects against Alzheimer's disease (AD) and Diabetes Mellitus. The pathogenesis of Alzheimer's disease and type 2 diabetes is closely related to amyloids (β-amyloid and amylin). Amyloid protein aggregates and then produces protein oligomers, which further aggregate to form fibers. These protein aggregates are cytotoxic, induces an oxidative reaction in cells to damage mitochondria, and triggers a cascade reaction such as vascular dementia reaction, causing damages to a large number of neurons and β cells, and ultimately leading to onset of Alzheimer's disease and type 2 diabetes. Oligomannaric acids target amyloid protein and antagonize the cascade reactions induced by the amyloid protein, and therefore have the effects of preventing and treating Alzheimer's disease and type 2 diabetes.

The prior document CN106344593A discloses the application of alginate oligosaccharide and its derivatives in the treatment of vascular dementia, and also discloses the pharmacodynamic activity of tetrasaccharide-to-decasaccharide mixture in the treatment of vascular dementia.

SUMMARY OF THE INVENTION

The invention relates to the use of a mannuronic diacid oligosaccharide composition in the treatment of vascular dementia. The present invention also relates to a method for treating vascular dementia, which comprises administering a therapeutically effective amount of the mannuronic diacid oligosaccharide composition of the present invention to a patient in need thereof.

The mannuronic diacid oligosaccharide composition used in the present invention has a specific composition, comprising mannuronic diacids having Formula (III) or a pharmaceutically acceptable salt thereof:

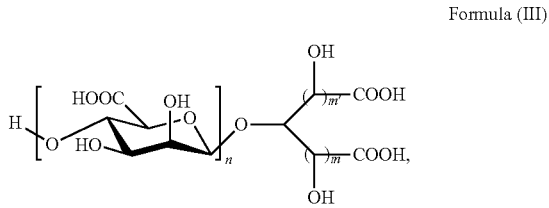

Formula (III)

wherein n is an integer selected from 1 to 9, m is selected from 0, 1 or 2, m' is selected from 0 or 1, and wherein, the total weight of mannuronic diacids wherein n=1–5 accounts for no less than 60% of the total weight of the composition;

the total weight of mannuronic diacids wherein n=1–2 accounts for less than 60% of the total weight of the composition.

DETAILED DESCRIPTION OF THE INVENTION

Figure 1:
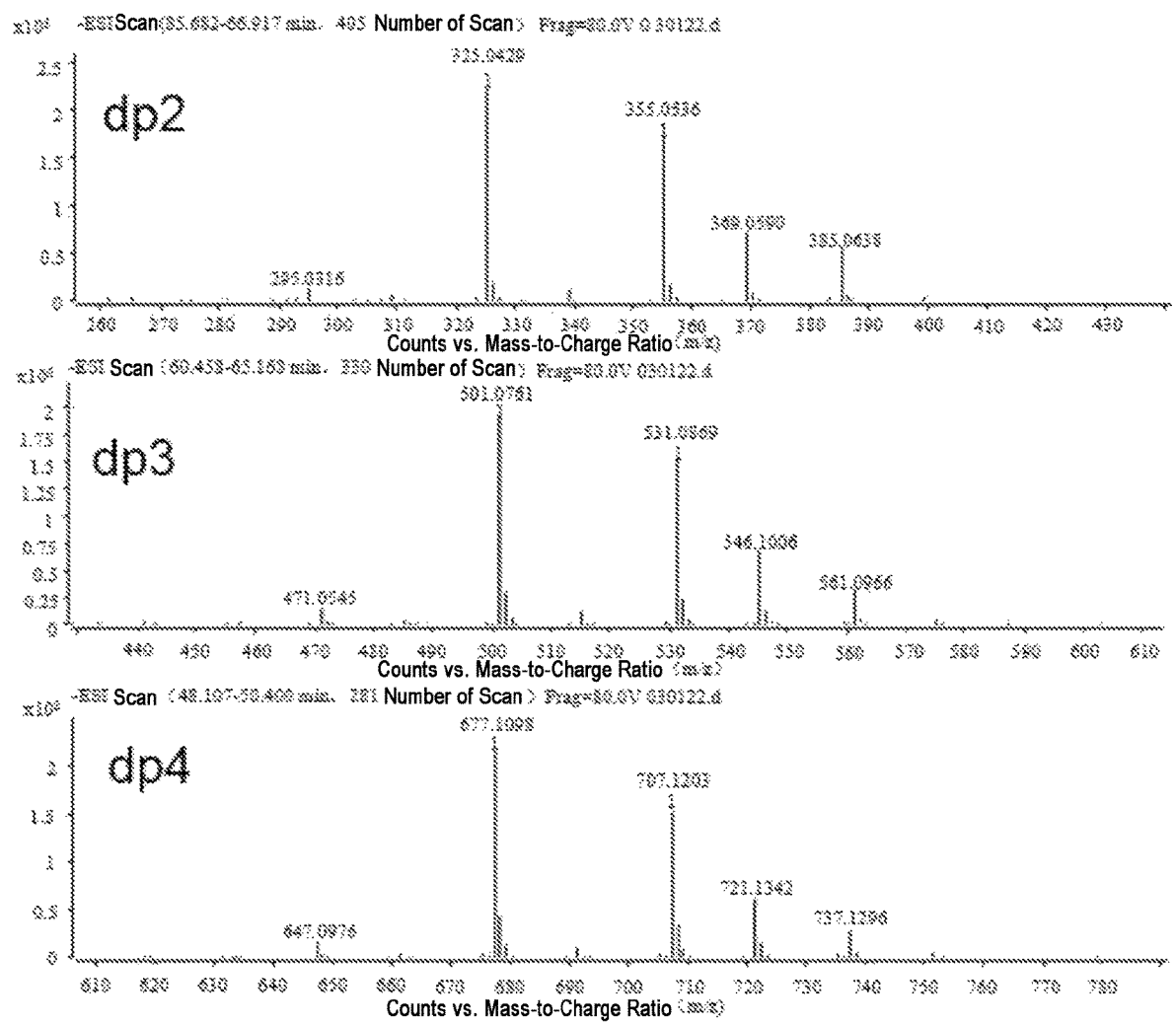
FIG. 1 shows mass spectra of disaccharide, trisaccharide and tetrasaccharide in product A.

Various aspects of the present invention will be described in detail below, but the present invention is not limited to these specific embodiments. Those skilled in the art can make some modifications and adjustments to the present invention according to the substantial disclosure below, and these adjustments are also within the scope of the present invention.

The present invention relates to the use of the mannuronic diacid oligosaccharide composition in the treatment of vascular dementia. The present invention also relates to a method of treating vascular dementia, comprising administering an effective amount of the mannuronic diacid oligosaccharide composition of the present invention to a patient in need thereof.

The mannuronic diacid oligosaccharide composition of the present invention comprises mannuronic diacids having Formula (III) or a pharmaceutically acceptable salt thereof:

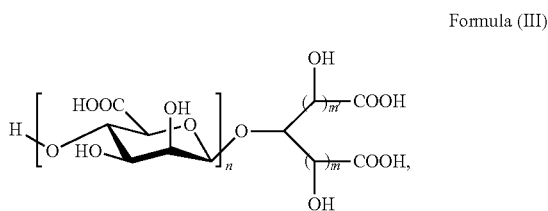

Formula (III)

wherein n is an integer selected from 1 to 9, m is selected from 0, 1 or 2, m' is selected from 0 or 1, and wherein, the total weight of mannuronic diacids wherein n=1–5 accounts for no less than 60% of the total weight of the composition;

the total weight of mannuronic diacids wherein n=1–2 accounts for less than 60% of the total weight of the composition.

The mannuronic diacid oligosaccharide composition of the present invention is a mixture of mannuronic diacids with different polymerization degrees, and the main components thereof are mannuronic diacid oligosaccharides with a polymerization degree of 2 to 10. The most active species in mannuronic diacids are tetrasaccharide to decasaccharide, especially hexasaccharide. However, the inventors currently find that adding a certain proportion of less active disaccharide to trisaccharide to the most active tetrasaccharide to decasaccharide does not reduce the biological activity and even increases the activity under the identical administration dosage in mass. Without being bound by any theory, it is speculated that this may be due to the synergistic effect of the small molecular weight disaccharide to trisaccharide when mixed with other oligosaccharides although they cannot work alone. However, when the proportion of disaccharide to trisaccharide is too high, the overall activity of the composition would be reduced. Therefore, the proportion of disaccharide to trisaccharide in the composition must be controlled within a certain range.

In the actual preparation process, a large amount of disaccharide to trisaccharide will be produced in the oxidative degradation reaction, and usually will be removed from the product after separation in order to avoid affecting the pharmaceutical effect of the product due to its low activity. However, based on the above findings of the inventors, it might not be required to separate and remove disaccharide to trisaccharide in the oxidative degradation products, and by controlling the conditions of the oxidative degradation reaction to control the proportion of disaccharide to trisaccharide within a certain range. The activity of the resulted composition can reach or even be better than that of the composition disclosed in the prior applications. Moreover, since disaccharide and trisaccharide are not considered as impurities to be removed, the product yield is also significantly higher than that disclosed in the prior applications. Thus, it greatly reduces the production cost, reduces the waste discharge, thereby being easier to realize in the actual production, and being easier to realize industrial large-scale production.

According to a preferred embodiment, in the mannuronic diacid oligosaccharide composition, the total weight of mannuronic diacids with m+m'=1 or 2 is no less than 50% of the total weight of the composition, preferably 60%-90%, more preferably 70%-90%. In particular, in the mannuronic diacid oligosaccharide composition, the total weight of mannuronic diacids with m+m'=1 is no less than 10% of the total weight of the composition, preferably 30-40%. In another preferred embodiment, in the mannuronic diacid oligosaccharide composition, the total weight of mannuronic diacids with m+m'=2 is no less than 10% of the total weight of the composition, preferably 30-50%.

According to a preferred embodiment, in the mannuronic diacid oligosaccharide composition, the total weight of mannuronic diacid oligosaccharide wherein n=1–5 accounts for 80-95% of the total weight of the composition.

According to a preferred embodiment, in the mannuronic diacid oligosaccharide composition, the total weight of mannuronic diacid oligosaccharide wherein n=1–2 accounts for 10-50% of the total weight of the composition, preferably 25-50%.

According to a preferred embodiment, in the mannuronic diacid oligosaccharide composition, the total weight of mannuronic diacid oligosaccharide wherein n=1–3 accounts for 20-70% of the total weight of the composition.

According to a preferred embodiment, in the mannuronic diacid oligosaccharide composition, the proportion of the total weight of mannuronic diacids wherein n=1–3 to the total weight of mannuronic diacids wherein n=4–7 is between 1.0 and 3.0.

According to a preferred embodiment, in the mannuronic diacid oligosaccharide composition, the weight percentage content of mannuronic diacids with each of the polymerization degrees in the above composition is: disaccharide 5-25%, trisaccharide 15-30%, tetrasaccharide 15-28%, pentasaccharide 5-25%, hexasaccharide 2-20%, heptsaccharide 2-20%, octasaccharide 2-20%, nonasaccharide 2-20%, and decasaccharide 2-20%. In particular, the weight percentage content of oligosaccharides in the composition is: disaccharide 5-25%, trisaccharide 15-30%, tetrasaccharide 15-28%, pentasaccharide 10-20%, hexasaccharide 5-15%, heptsaccharide 3-10%, octasaccharide 2-5%, nonasaccharide 1-5%, and decasaccharide 1-5%. More preferably, the weight percentage content of oligosaccharides in the composition is: disaccharide 10-20%, trisaccharide 18-30%, tetrasaccharide 15-28%, pentasaccharide 15-20%, hexasaccharide 5-10%, heptsaccharide 3-5%, octasaccharide 2-5%, nonaccharide 1-3%, and decasaccharide 1-3%.

In the mannuronic diacid oligosaccharide composition of the present invention, the pharmaceutically acceptable salt thereof is sodium salt or potassium salt.

The inventors of the present patent application have found that, when the above nine oligosaccharides having new structures are compounded according to certain proportions, a high-activity oligosaccharide composition can be obtained, of which the activity is higher than that of the most active hexasaccharide. In particular, the composition added with a certain proportion of disaccharide and trisaccharide has higher activity than the composition without disaccharide and trisaccharide. The proportion of each oligosaccharide in the high-activity oligosaccharide composition needs to be combined according to the following proportion:

The total weight of mannuronic diacids wherein n=1–5 in the composition accounts for no less than 60% of the total weight of the composition, preferably 80-95%. The total weight of mannuronic diacids wherein n=1–2 accounts for less than 60% of the total weight of the composition, preferably 10-50%, more preferably 25-50%. The total weight of mannuronic diacid oligosaccharide wherein n=1–3 accounts for 20-70% of the total weight of the composition. The ratio of the total weight of the mannuronic diacid oligosaccharide wherein n=1–3 to the total weight of the mannuronic diacid oligosaccharide wherein n=4–7 is between 1.0 and 3.5, preferably between 1.0 and 3.0.

The medicament for the treatment of vascular dementia of the present invention comprises a mannuronic diacid oligosaccharide composition, which comprises mannuronic diacids having Formula (III) or pharmaceutically acceptable salts thereof, and one or more pharmaceutically acceptable carriers. The medicament of the present invention can be in the form of tablets, hard capsules, soft capsules, enteric capsules, microcapsules, granules, syrups, injections, granules, emulsions, suspensions, solutions and sustained-release formulation for oral or non-oral administration.

The pharmaceutically acceptable carrier of the present invention refers to a pharmaceutically acceptable carrier known to those skilled in the art. The pharmaceutically acceptable carrier of the present invention includes, but is not limited to, fillers, wetting agents, binders, disintegrants, lubricants, adhesive, glidants, taste masking agents, surfactants, preservatives, etc. Fillers include, but are not limited to lactose, microcrystalline cellulose, starch, saccharide powder, dextrin, mannitol, calcium sulfate, etc. Wetting agents and binders include, but are not limited to sodium carboxymethylcellulose, hydroxypropyl cellulose, hydroxypropyl methylcellulose, gelatin, sucrose, polyvinylpyrrolidone, etc. Disintegrants include, but are not limited to sodium carboxymethyl starch, crosslinked polyvinylpyrrolidone, crosslinked sodium carboxymethyl cellulose, low substituted hydroxypropyl cellulose, etc. Lubricants include, but are not limited to, magnesium stearate, silica gel micropowder, talc, hydrogenated vegetable oil, polyethylene glycol, magnesium lauryl sulfate, etc. Adhesive includes, but are not limited to, Arabic gum, alginic acid, calcium carboxymethylcellulose, sodium carboxymethylcellulose, glucose binders, dextrins, dextrose, ethyl cellulose, gelatin, liquid glucose, guar gum, hydroxyethylcellulose, hydroxypropyl cellulose, hydroxypropyl methylcellulose, magnesium aluminum silicate, maltodextrin, methylcellulose, polymethacrylates, polyvinylpyrrolidone, pregelatinized starch, sodium alginate, sorbitol, starch, syrup, and tragacanth gum. Glidants include, but are not limited to colloidal silica, powdered cellulose, magnesium trisilicate, silica and talc. Taste masking agents include, but are not limited to, aspartame, stevioside, fructose, glucose, syrup, honey, xylitol, mannitol, lactose, sorbitol, maltitol, and glycyrrhizin. Surfactants include, but are not limited to Tween-80 and poloxamer. Preservatives include, but are not limited to, parabens, sodium benzoate, potassium sorbate, etc.

As used herein, the term "treatment" generally refers to achieving a desired pharmacological and/or physiological effect. This effect can be preventive according to the complete or partial prevention of the disease or its symptoms; and/or can be therapeutic according to partial or complete stabilization or cure of the disease and/or side effects due to the disease. As used herein, "treatment" covers any treatment of a patient's disease, including: (a) prevention of diseases or symptoms occurring in patients who are susceptible to diseases or symptoms but have not yet been diagnosed with the disease; (b) inhibiting the symptoms of the disease, i.e. preventing its development; or (c) relieving the symptoms of the disease, i.e. causing the disease or the deterioration of the symptoms.

Mannuronic Diacid Oligosaccharide Composition

The mannuronic diacid oligosaccharide composition for the treatment of vascular dementia of the present invention comprises mannuronic diacids having Formula (III) or a pharmaceutically acceptable salt thereof:

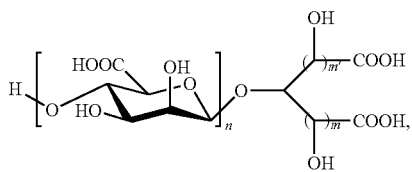

Formula (III)

wherein n is an integer selected from 1 to 9, m is selected from 0, 1 or 2, m' is selected from 0 or 1, and wherein, the total weight of mannuronic diacids wherein $n=1-5$ accounts for no less than 60% of the total weight of the composition;

the total weight of mannuronic diacids wherein $n=1-2$ accounts for less than 60% of the total weight of the composition.

In an exemplary embodiment, the preparation method of the mannuronic diacid oligosaccharide composition for the treatment of vascular dementia comprises the following steps:

(1) Preparation of the Mannuronic Diacids Products:

Preparation of M segment intermediate. As described above, the raw material M-segment intermediate used in the present invention can be prepared by a method known in the prior art, e.g., the methods disclosed in Chinese Patent Application No. 98806637.8 and CN02823707.2. A common method can be simply described below: alginic acid is preliminarily degraded to give mixed polysaccharides of polymannuronic acid and polyguluronic acid; then the mixed polysaccharides are subjected to acidic precipitation to remove the polyguluronic acid therein, and further refinement is conducted to obtain a homopolymannuronic acid with a purity of more than 90%, i.e., an M-segment intermediate.

Ozone oxidative degradation. The M-segment intermediate is dissolved in an appropriate amount of water and stirred at room temperature or under heating condition. With continuous introduction of ozone, the reaction starts. The pH value of the reaction can be adjusted to by dropwise adding dilute hydrochloric acid or dilute NaOH solution 3-13, preferably to 4-10, more preferably to 6-8. The temperature is preferably 0-70° C., more preferably 10-45° C. After the completion of the reaction, the introduction of ozone is stopped and the pH is adjusted to neutral.

Membrane separation and purification. The reaction product obtained above is formulated into a solution at a concentration of about 10% and separated by a molecular cut-off membrane to remove degradation products below monosaccharide. The retentate is collected. The MWCO of the molecular cut-off membrane used is 1000 Da-3000 Da, preferably 2000 Da. The collected liquid is concentrated on a rotary evaporator and dried under vacuum to obtain an oligomannuronic diacid mixture. After analysis, it is found that these products are all compositions of oligosaccharide from disaccharide to decasaccharide with contents being within certain proportion ranges. This method is exemplarily shown in examples 1-3.

(2) Preparation of Oligosaccharides with a Single Polymerization Degree

The oligosaccharide mixture obtained in step (1) is dissolved to a concentration of about 10%, separated on a P6 gel chromatographic column, and subjected to ultraviolet detection to collect each effluent component. The components having the same polymerization degree are combined. Nine components of disaccharide to decasaccharide were collected, respectively desalted by G10 gel column chromatography, concentrated by rotary evaporator, and dried in vacuum. A specific purification and preparation process is shown in example 4. The operations such as column chromatography, desalting and drying are known to those skilled in the art.

The pharmacological activities of the oligosaccharides with single polymerization degree were evaluated in anti-vascular dementia animal models, and it was found that hexasaccharide is most active.

(3) Activity Comparison of Oligosaccharide Compositions

The oligosaccharide composition is compared with the purified hexasaccharide for the pharmacological activity. The results show that the oligosaccharide composition of the present invention and the comparative experimental samples are significantly better than the most active hexasaccharide in the oligosaccharides with single polymerization degree, while the activity of the composition comprising disaccharide and trisaccharide is slightly lower than that of hexasaccharide. Without being bound by any theory, it is believed that the oligosaccharides can play a synergistic effect after being compounded. When the proportion of disaccharide to hexasaccharide in the composition is no less than 60%, and the proportion of disaccharide to trisaccharide is less than 60%, the activity of the composition is the highest. However, when the proportion of disaccharide to trisaccharide is more than 60%, the activity of the composition would also decrease.

Animal Model and Steps for Evaluating Pharmacodynamic Activity

1. Animal model for anti-vascular dementia pharmacodynamic evaluation—a mouse model with vascular dementia caused by bilateral common carotid artery occlusion (BCCAo)

The bilateral common carotid artery occlusion (BCCAo) model is a commonly used vascular dementia model in the field established by global cerebral ischemia and reperfusion.

1.1 Animal Grouping and Administration

Male C57BL/6 mice, weighing 22±2 g were chosen and randomly divided into groups: sham operation group, 30-minute bilateral common carotid artery occlusion (BCCAo) model group (abbreviated as 30-min BCCAo group), and dosing group, wherein there are 10 animals in each group. After the animals were divided into groups, mice in the sham operation group and 30-min BCCAo group were given intragastrically distilled water, once a day, for 5 consecutive days, followed by BCCAo surgery. Mice in the dosing group were dosed intragastrically with the corresponding drugs, once a day, for 5 consecutive days, followed by BCCAo surgery. The BCCAo surgery was to anesthetize each group of mice with pentobarbital sodium; separate and occlude the bilateral common carotid arteries of the mice in the model group and the dosing group for 30 minutes, then remove the occlusion and suture the neck wound. For the sham operation group, the bilateral common carotid arteries were not occluded after separation, and the neck incision was directly sutured. Twenty-four hours after BCCAo, mice in each group continued to be given intragastrically the corresponding drugs or distilled water according to the preoperative dosing schedule, for further 23 consecutive days of administration. The darkness avoidance test was performed on the 7th day after BCCAo, and the Morris water maze test was started on the 13th day to evaluate the improvement effect of the mannuronic diacid composition on the learning and memory ability of mice. After the behavioral test, the mice were sacrificed, and the brain tissues were fixed. The neuronal damage in the hippocampus of the mice after BCCAo and the protective effect of the mannuronic diacid composition on the injured neurons were evaluated by the methods such as HE staining.

1.2 Darkness Avoidance Test

The darkness avoidance test is used to test the learning and memory abilities of mice in spatial discrimination. The memory impairment of spatial positioning can only appear when the hippocampus or the area around the hippocampus is damaged. The dark-avoidance experimental box is a device designed to take advantage of the habit of following darkness and avoiding light in mice. Half of the box is a dark room and the other half is a bright room, with a small hole in the middle for connection. The bottom of the dark room is covered with a live copper grid. Animals are subject to electrical shock when they enter the dark room, and escape back to the light room. After the animals are trained for 24 hours, the test is performed again. The latency in the darkness avoidance test refers to the time from when the animal is placed in the light room to the first time it enters the dark room. The longer the latency in the darkness avoidance test is and the fewer the number of avoidance errors is, the better the animal memory is.

1.3 Morris Water Maze Behavior Assay

The Morris water maze (MWM) test is an experiment in which experimental animals are forced to swim and learn to find platforms hidden in the water. It is mainly used to test the experimental animals' ability of learning and memory in terms of spatial position and direction (spatial positioning). The mouse Morris water maze is mainly composed of a cylindrical pool with a diameter of 80 cm and a height of 70 cm and a movable platform with a diameter of 8 cm. The digital camera in the space above the pool is connected to a computer. Before the test, clean water is poured into the pool in advance. The water depth is 15 cm, and the water surface is 0.5 cm above the surface of the platform. Milk is added to make the pool water opaque. The position of the platform remains unchanged during the test. Morris water maze behavior includes the following two test indicators.

(1) The place navigation test is used to measure the ability of mice to learn the water maze and acquire memory. The test was started on the 13th day after BCCAO and lasted 4 days. The mice were trained once both in the morning and in the afternoon, totally 8 times. During training, the mouse enters the pool at ½ arc in the west quadrant, and enters the water with its head toward the pool wall. If the platform is not found within 120 seconds, the experimental staff will lead it to the platform and leave it for 30 seconds to guide its learning and memory. The route map and the time required for the mice to find and climb on the platform are observed and recorded, i.e., recording their escape latency and swimming speed in Morris water maze test. The escape latency in the Morris water maze test refers to the time from when the mouse enters the water to find the platform. The shorter the escape latency in the Morris water maze test is, the better the animal memory is.

(2) Spatial probe test is used to measure the ability of mice to retain the memory of the platform's spatial location after learning to find the platform. After the place navigation test was finished, the platform was removed at 1 day intervals. The mice were put into the water from the same entry point, and the number of times they crossed the original platform was measured. Data acquisition and processing were completed by the image automatic monitoring and processing system.

2. Animal model for anti-vascular dementia pharmacodynamic evaluation—a rat model with vascular dementia caused by middle cerebral artery occlusion (MCAO)

The middle cerebral artery occlusion (MCAO) model is a vascular dementia model commonly used in the field established by focal cerebral ischemia.

2.1 Animal Grouping and Administration

Male Wistar rats were chosen and randomly divided into groups: blank control group, sham operation group, model group (MCAO group), and dosing group, wherein there are 10 animals in each group. Animals in the blank group, sham operation group, and MCAO group were orally given distilled water, and the alginate oligosaccharide group were all orally given the corresponding dose of alginate oligosaccharide. After 7 days of continuous administration in each group, except for the rats in the blank group, the rats in the other groups were anesthetized by intraperitoneal injection of 350 mg/kg chloral hydrate, and fixed on the rat board in the left lateral position. Under an operating microscope, the skin was incised along the midpoint of the connection between the external auditory canal and the eye canthus to expose the zygomatic arch. The distance between the phosphate bone and the mandible was spread using a small distractor. A 2 mm×2 mm bone window was opened at the base of the skull. The dura mater was opened to expose the middle cerebral artery, and one side of the middle cerebral artery was coagulated by high-frequency electrocautery to cause local cerebral ischemia (the animals in the sham operation group only exposed the middle cerebral artery without coagulation). The incision was sutured layer by layer. The room temperatures during and after the operation were strictly controlled at 24~25° C. After surgery, the drug or distilled water were continued to give to each group according to the preoperative dosing schedule. The Morris water maze test was performed for each group on the 11th day after the surgery.

In this experiment, rats in each group were trained once a day for 5 consecutive days, i.e., place navigation test. The time it took for the animals to find the platform (i.e., the escape incubation period in the Morris water maze test) was recorded. Those who failed to find the platform for about 120 seconds were guided to swim toward the platform in a straight line and stand on the platform for 30 seconds to induce learning and memory. After the place navigation test was finished, the platform was removed at 1 day intervals. The rats were put into the water from the entry point, and the time they first reached the original platform and the number of times they crossed the original platform were recorded, i.e., spatial probe test. The learning and memory function of animals were evaluated. The escape latency in the Morris water maze test refers to the time from when the rat enters the water to find the platform. The shorter the escape latency in the Morris water maze test is, the better the animal memory is.

Advantages of the present invention are further illustrated in the following nonlimiting examples. However, the specific materials and amounts thereof as well as other experimental conditions used in the examples should not be construed as limiting the present invention. Unless otherwise specified, the parts, proportions, percentages, and the like in the present invention are all calculated by mass.

EXAMPLE

Example 1

Step 1): Preparation of a Mannuronic Diacid Oligosaccharide Mixture

An M-segment intermediate was prepared by the method disclosed in prior patents. The specific operations are briefly described below: 5 Kg of sodium alginate was formulated into a solution of about 10%, and the pH was adjusted to about 3.0 by adding dilute hydrochloric acid. The solution was heated to 80° C., and stirred. It was allowed to react for 10 hr before the heating was stopped. After cooling to room temperature, the pH was adjusted to 9.0 by adding NaOH, and further adjusted to 2.85 by adding dilute hydrochloric acid. The solution was centrifuged at 5000 rpm for 10 min. The supernatant was collected, and adjusted to pH 1.0 by adding HCl. After centrifugation, the precipitate was collected, concentrated on a rotary evaporator, and dried under vacuum to give 1500 g of the M-segment intermediate. 500 g of the M-segment intermediate was weighed, and dissolved in distilled water to prepare a solution in a volume of 5 L. The solution was adjusted to pH 6.5 with NaOH, and heated in a water bath to control the reaction temperature at 75° C. The gas flow rate at the outlet of an oxygen cylinder and the power of an ozone generator were adjusted such that ozone was fed into the reaction solution at a mass concentration flow rate of 8 g/hr. After 4 hr of reaction, the feeding of ozone was stopped, and a suitable amount of water was added to adjust the concentration of the solution to about 10%. The solution was filtered through an ultrafiltration membrane with a molecular weight cut-off of 2,000 Da to collect a retentate. The collected liquid was concentrated on a rotary evaporator and dried under vacuum to obtain 350 g of mannuronic diacid product A.

Step 2): Analysis of Proportions and Structures of Oligosaccharides with Various Polymerization Degrees in Mannuronic Diacid Product A 100 mg of the above dried mannuronic diacid product A was accurately weighed, dissolved in water to a concentration of 10 mg/mL, and passed through a 0.22 μm filter membrane to obtain a test sample solution. The proportions of oligosaccharides with different polymerization degrees in the composition were determined by Superdex peptide molecular exclusion chromatography (GE Co.) in combination with multi-angle laser light scattering (MALS, Wyatt Co.). The experimental conditions were as follows:

Chromatographic column: Superdex peptide 10/300G1
Mobile phase: 0.1 mol/L NaCl
Injection volume: 10 μL
Flow rate: 0.3 mL/min Test results: from disaccharide to decasaccharide were represented by dp2-dp10, respectively, dp2 was 19%, dp3 was 25%, dp4 was 22%, dp5 was 13%, dp6 was 9%, dp7 was 6%, dp8 was 3%, dp9 was 2% and dp10 was 1%.

Step 3): LC-MS Analysis of Structures of Oligosaccharides with Various Polymerization Degrees in Mannuronic Diacid Product A Experimental conditions:
Chromatographic column: Superdex peptide 10/300G1
Mobile phase: 20% methanol+80% 80 mmol/L $NH_4Ac$
Flow rate: 0.1 mL/min
Column temperature: 25° C.±0.8° C.

Mass spectrometry conditions: Agilent 6540 QTOF; ion source: ESI collision voltage 120 V; negative ion mode. The width of the acquired signal (m/z) was 100-1000.

Figure 2:
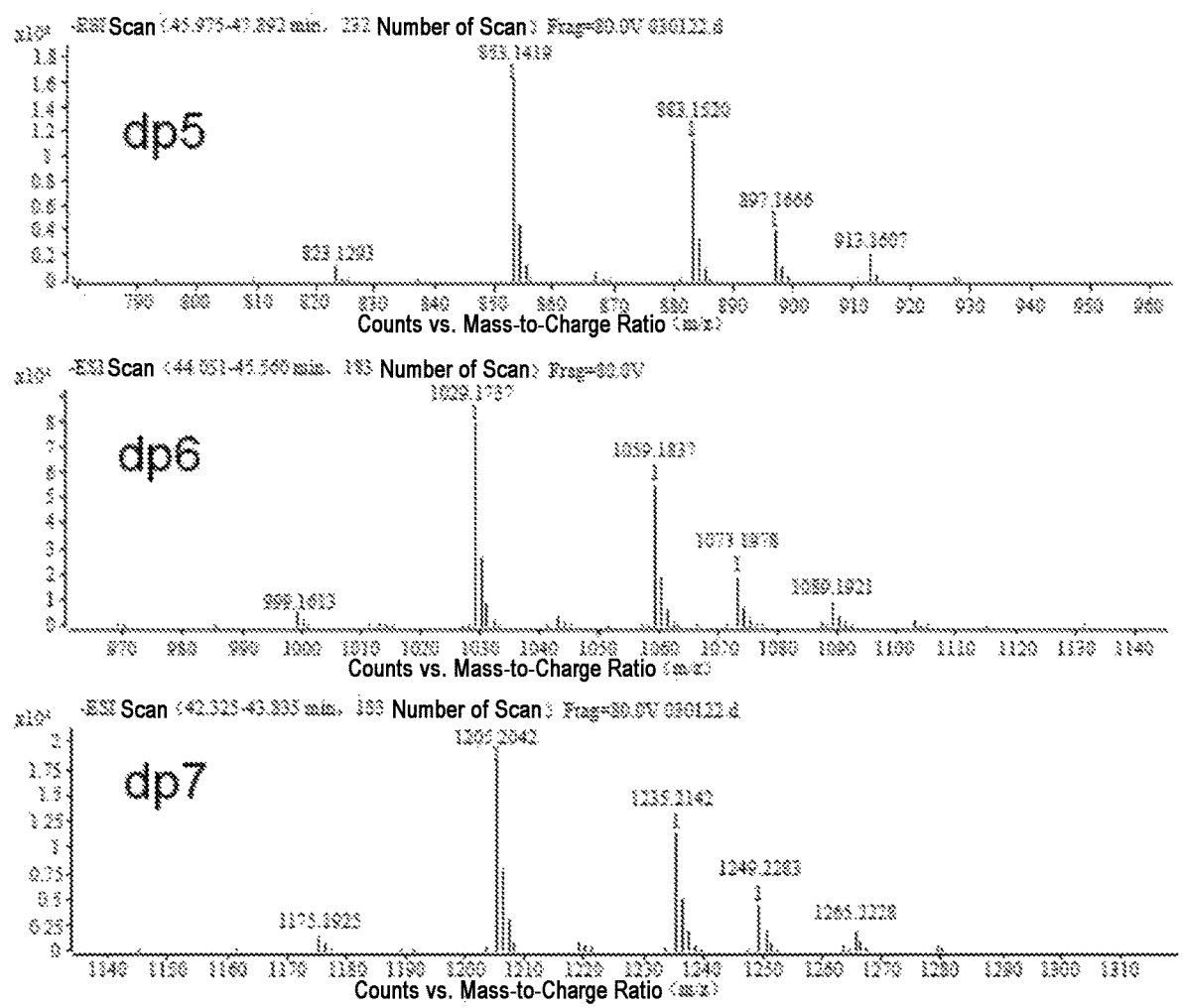
FIG. 2 shows mass spectra of pentasaccharide, hexasaccharide and heptasaccharide in product A.
Figure 3:
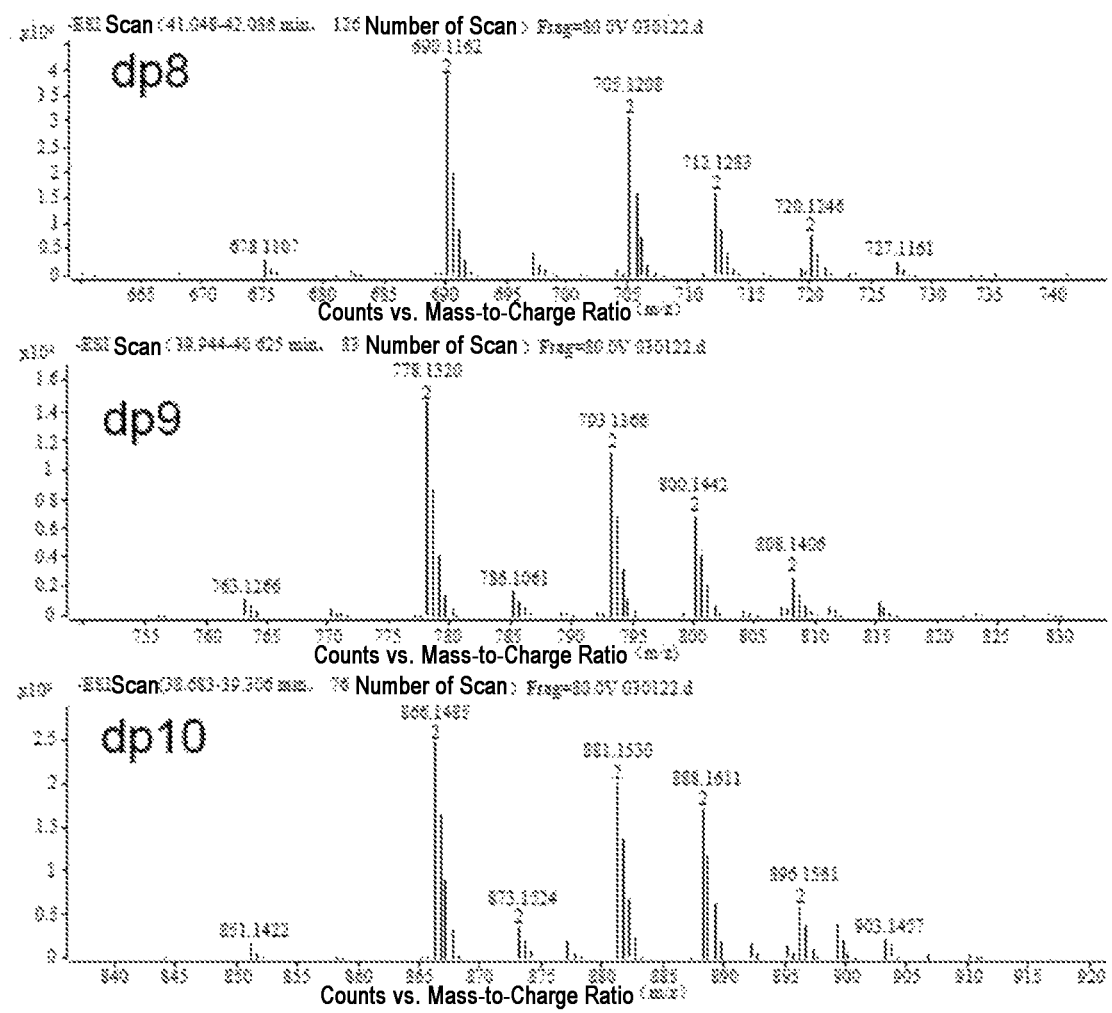
FIG. 3 shows mass spectra of octasaccharide, nonasaccharide and decasaccharide in product A.

The mass spectra of oligosaccharides with various polymerization degrees are shown in FIGS. 1-3. Various signal peaks in the mass spectra were assigned, confirming the molecular structure of all oligosaccharides in product A, i.e., the structure shown in General Formula (III). See Table 1 below for the signal assignments and the structures corresponding to the signals.

TABLE 1 six diacid structures in oligosaccharides with different polymerization degrees in product A and their mass-to-charge ratios in mass spectra

| No. | Molecular structure | Molecular Formula | Mass-to-Charge Ratio (m/z) | | | | |
|---|---|---|---|---|---|---|---|
| | | | n = 1 $[M - 1]^-$ | n = 2 $[M - 1]^-$ | n = 3 $[M - 1]^-$ | n = 4 $[M - 1]^-$ | n = 5 $[M - 1]^-$ |
| 1 | [structure] | $(C_6H_8O_6)_nC_6H_{10}O_8$ n = 1-9 | 385 | 561 | 737 | 913 | 1089 |
| 2 | [structure] | $(C_6H_8O_6)_nC_5H_8O_7$ n = 1-9 | 355 | 531 | 707 | 883 | 1059 |

TABLE 1-continued six diacid structures in oligosaccharides with different polymerization degrees in product A and their mass-to-charge ratios in mass spectra

| No. | Structure | Formula | | | | |
|---|---|---|---|---|---|---|
| 3 | [structure] | $(C_6H_8O_6)_nC_5H_8O_7$ n = 1-9 | 355 | 531 | 707 | 883 | 1059 |
| 4 | [structure] | $(C_6H_8O_6)_nC_4H_6O_6$ n = 1-9 | 325 | 501 | 677 | 853 | 1029 |
| 5 | [structure] | $(C_6H_8O_6)_nC_4H_6O_6$ n = 1-9 | 325 | 501 | 677 | 853 | 1029 |
| 6 | [structure] | $(C_6H_8O_6)_nC_3H_4O_5$ n = 1-9 | 295 | 471 | 647 | 823 | 999 |

| | Mass-to-Charge Ratio (m/z) | | | |
|---|---|---|---|---|
| No. | n = 6 $[M - 1]^-$ | n = 7 $[M - 2]^{2-}$ | n = 8 $[M - 2]^{2-}$ | n = 9 $[M - 2]^{2-}$ |
| 1 | 1265 | 720 | 808 | 896 |
| 2 | 1235 | 705 | 793 | 881 |
| 3 | 1235 | 705 | 793 | 881 |
| 4 | 1205 | 690 | 778 | 866 |
| 5 | 1205 | 690 | 778 | 866 |
| 6 | 1175 | 675 | 763 | 851 |

It was found from the above mass spectrometric structural analysis that the mannuronic acid at the reducing end of the sugar chain in product A was oxidized to a saccharic diacid structure (see General Formula III for the structure), which could be a mannaric diacid structure comprising 6 carbon atoms (m+m'=3) with a content of about 10%~30%, or a decarboxylation product of mannaric diacid, i.e., a saccharic diacid comprising 5 carbons (m+m'=2) (30~50%) and a saccharide diacid with 4 carbons (m+m'=1) (30%~40%).

Example 2

100 g of the M-segment intermediate in example 1 was weighed, and dissolved in distilled water to prepare a solution with a volume of 0.8 L. The solution was adjusted to pH 4.0 with NaOH, and the reaction was carried out at room temperature (25° C.). The gas flow rate at the outlet of an oxygen cylinder and the power of an ozone generator were adjusted such that ozone was fed into the reaction solution at a mass concentration flow rate of 1 g/hr. After 10 hr of reaction, the feeding of ozone was stopped, and a suitable amount of water was added to adjust the concentration of the solution to about 15%. The solution was filtered through an ultrafiltration membrane with a molecular weight cut-off of 1,000 Da to collect a retentate. The collected liquid was concentrated on a rotary evaporator and dried under vacuum to obtain 80 g of mannuronic diacid product B.

The proportions of oligosaccharides components with various polymerization degrees in B were determined by Superdex peptide molecular exclusion chromatography (GE Co.) in combination with multi-angle laser light scattering (MALS, Wyatt Co.). The measurement method was the same as the relevant part in example 1. Test results: from disaccharide to decasaccharide were represented by dp2-dp10, respectively, dp2 was 20%, dp3 was 25%, dp4 was 19%, dp5 was 12%, dp6 was 9%, dp7 was 5%, dp8 was 5%, dp9 was 3% and dp10 was 2%.

Example 3

100 g of the M-segment intermediate of example 1 was weighed, dissolved in distilled water to prepare a solution with a volume of 1.5 L. The solution was adjusted to pH 9.0 with NaOH, and the reaction was carried out in a water bath at 45° C. The gas flow rate at the outlet of an oxygen cylinder and the power of an ozone generator were adjusted such that ozone was fed into the reaction solution at a mass concentration flow rate of 3 g/hr. After 2 hr of reaction, the feeding of ozone was stopped, and a suitable amount of water was added to adjust the concentration of the solution to about 5%. The solution was filtered through an ultrafiltration membrane with a molecular weight cut-off of 3,000 Da to collect a retentate. The collected liquid was concentrated on a rotary evaporator and dried under vacuum to obtain 60 g of mannuronic diacid product C.

The proportions of oligosaccharides with various polymerization degrees in C were determined by Superdex peptide molecular exclusion chromatography (GE Co.) in combination with multi-angle laser light scattering (MALS, Wyatt Co.). The measurement method was the same as the relevant part in example 1. Test results: from disaccharide to decasaccharide were represented by dp2-dp10, respectively, dp2 was 8%, dp3 was 20%, dp4 was 28%, dp5 was 19%, dp6 was 13%, dp7 was 6%, dp8 was 3%, dp9 was 2%, and dp10 was 1%.

Example 4

Preparation of Mannuronic Diacid Oligosaccharide with Single Polymerization Degree, which was as Follows:

1. Sample preparation: 300 g of mannuronic diacid product A prepared in example 1 was weighed, dissolved in water, prepared into 1000 mL of concentrated solution, and placed in a refrigerator at 4° C. for use. For each use, 50 mL was taken out and was 1:2 diluted with water, and then suction filtered through a 0.22 μm ultrafiltration membrane.

2. Chromatographic separation conditions: The chromatograph was AKTA pure 150 (purchased from GE Co.) equipped with a UV detector and an automatic collector. Separation chromatographic column: 1.2 kg of BioGel P6 (purchased from Bio-Rad Co.) was mixed with deionized water, vacuum degassed, manually filled into a glass column (inner diameter: 10 cm), rinsed with 10 column volumes of pure water. The chromatographic column bed was stable and the height was 1.0 m. Then, the mobile phase was changed to a 0.02 M NaCl solution, and after equilibration with 10 column volumes, sample loading was initiated.

3. Sample loading and separation: The flow rate of the pump was set at 1 mL/min. After 100 mL of the sample solution was pumped to the top of the column through the chromatograph's own pump, it was switched to the mobile phase and eluted at a flow rate of 5 mL/min. After outflow of the dead water volume, automatic collection was initiated and 50 mL was collected per tube.

4. The sample loading was repeated, and after 20 repetitions of preparation, the same fractions were combined, concentrated on a rotary evaporator, and lyophilized to obtain a total of 9 oligosaccharides with single polymerization degree from disaccharide to decasaccharide.

Example 5

A pharmacological activity evaluation was conducted between the compositions and hexasaccharide to examine the synergistic effect of the oligosaccharides with different polymerization degrees in the compositions and the range of proportions of the oligosaccharides.

Sample Preparation:

(1) Composition Product D:

The mannuronic diacid oligosaccharides with single polymerization degree as prepared in example 4 were accurately weighed from disaccharide to decasaccharide by the polymerization degree. The weight of each saccharide taken out was as follows: 3.0 g of disaccharide, 3.0 g of trisaccharide, 1.5 g of tetrasaccharide, 1.5 g of pentasaccharide, 0.4 g of hexasaccharide, 0.2 g of heptasaccharide, 0.2 g of octasaccharide, 0.1 g of nonasaccharide, and 0.1 g of decasaccharide. They were uniformly mixed to obtain 10 g of composition product D.

(2) Preparation of Comparative Experimental Samples

A tetrasaccharide-to-decasaccharide containing mixture was prepared by referring to the methods disclosed in examples 1 and 2 of the prior patent document CN106344592A.

1 g of sodium polymannuronate (weight average molecular weight 8235 Da, provided by Shanghai Green Valley Pharmaceutical Co., Ltd.) was weighed and added with appropriate amount of distilled water to prepare 1% (weight percent) aqueous solution of sodium polymannuronate. The pH value of the 1% aqueous solution of sodium polymannuronate was adjusted to 4 with hydrochloric acid, and then the aqueous solution was placed in an autoclave. The reaction was subjected to heating at 110° C. for 4 hours. The reacted solution was removed from the autoclave and allowed to cool. After cooling, the pH value of the reacted solution was adjusted with NaOH solution to obtain neutral liquid. Under the condition of stirring, the neutral liquid was slowly added into ethanol with a volume of 4 times the volume of the liquid. The alcohol precipitation was carried out, and the solution was left to stand overnight. The solid substance obtained by alcohol precipitation was filtered and separated, and the absolute ethanol was used to wash the solid substance obtained from filtering and separation during the filtering and separation process. Finally a white filter cake was produced. The filter cake was filtered in an oven at 60° C. to obtain crude alginate oligosaccharide.

5 g of crude alginate oligosaccharide was prepared into a 5% (weight percentage) aqueous solution. The fresh oxidant copper hydroxide was prepared by adding 25 ml of 5% (weight percent) copper sulfate solution to 50 ml of 10% (weight percent) sodium hydroxide solution and mixing immediately. The fresh oxidant copper hydroxide was immediately added to 40 ml of the above 5% (weight percent) alginate oligosaccharide solution, while heated in a boiling water bath until no more brick red precipitates were produced. The reaction system was centrifuged to remove the precipitate to obtain the supernatant. A little supernatant was added to the oxidant again to check whether there was still brick red precipitate produced. If brick red precipitate was still produced, all the supernatants obtained from the centrifugation would continue to react with other part of the oxidant until it was checked that no brick red precipitates were produced. The final reaction system was centrifuged to obtain the supernatant. 4 times the volume of 95% ethanol was added to the supernatant for alcohol precipitation, and the solution was allowed to stand overnight. The solid substance given by alcohol precipitation was filtered and separated, and the solid substance was washed with absolute ethanol. The obtained solid substance was placed in an oven at 60° C. and dried to give the crude alginate oligosaccharide represented by Formula (II).

1 g of the crude alginate oligosaccharide was prepared into a 10% (weight percent) aqueous solution, and alcohol precipitation was carried out again by using a 95% ethanol solution. The precipitate obtained by alcohol precipitation again was filtered and separated, followed by optionally washing with absolute ethanol. The precipitate was separated and dried to obtain a solid substance. The solid substance was prepared into a 5% (weight percentage) aqueous solution. The aqueous solution was filtered with a 3 μm pore size membrane and the filtrate was collected. The filtrate was eluted and separated on a molecular exclusion chromatography Bio-Gel-P6 gel column (1.6×180 cm, available from Bio-Rad Company). The eluent as mobile phase was 0.2 mol L-1NH$_4$HCO$_3$. Eluate from the column chromatography was sequentially collected by a plurality of 5 ml test tubes, and then the saccharide content of the eluate in each test tube was detected by using a sulfuric acid-carbazole method. According to the detection results, eluates containing alginate oligosaccharide components with different molecular weights were respectively collected according to the detection results. Eluents containing alginate oligosaccharide components with different molecular weights were respectively concentrated under reduced pressure and lyophilized. Component 1 was discarded to obtain alginate oligosaccharide components 2-12 shown in Formula (II) (n has a value of 0-10 respectively) with different molecular weights, and alginate oligosaccharide eluent shown in Formula (II) with n=2-8 was collected, combined and dried. Alginate oligosaccharide mixture (tetrasaccharide to decasaccharide mixture) shown in Formula (II) with n=2-8 was produced as a comparative experimental sample.

The proportion of oligosaccharide components with various polymerization degrees in comparative experimental samples was detected by using Superdex peptide (GE Co.) molecular exclusion chromatography combined with multi-angle laser scattering (MALS, Wyatt). The determination method is the same as the relevant part in example 1. Test results: tetrasaccharide to decasaccharide is represented by dp4-dp10, which is 10% dp4, 12% dp5, 13% dp6, 14% dp7, 15% dp8, 19% dp9 and 17% dp10, respectively.

Products A, B and C respectively prepared in examples 1, 2 and 3, product D in this example and oligosaccharide proportions in the comparative experimental samples are shown in Table 2 below.

TABLE 2 percentages of oligosaccharides in mannuronic diacid oligosaccharides composition products and comparative experimental samples.

| Composition | Proportion | | | | | | | | |
|---|---|---|---|---|---|---|---|---|---|
| | Di- | Tri- | Tetra- | Penta- | Hexa- | Hepta- | Octa- | Nona- | Deca- |
| A | 19% | 25% | 22% | 13% | 9% | 6% | 3% | 2% | 1% |
| B | 20% | 25% | 19% | 12% | 9% | 5% | 5% | 3% | 2% |
| C | 8% | 20% | 28% | 19% | 13% | 6% | 3% | 2% | 1% |
| D | 30% | 30% | 15% | 15% | 4% | 2% | 2% | 1% | 1% |
| Comparative samples | 0 | 0 | 10% | 12% | 13% | 14% | 15% | 19% | 17% |

10 g of each of the above four samples A, B, C and D was taken out. The pharmacological activities of these compositions with hexose (6T) and comparative experimental samples were compared according to the method described in "animal model for anti-vascular dementia pharmacodynamic evaluation".

1. A Mouse Model of Vascular Dementia Caused by Bilateral Common Carotid Artery Occlusion (BCCAo)

1.1 Test Results of the Darkness Avoidance Experiment

Figure 4:
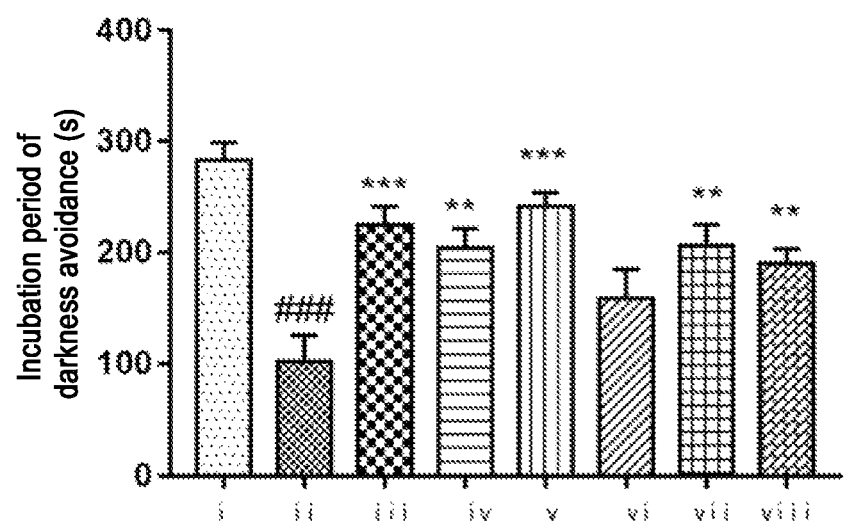
FIG. 4 shows the effects of oligosaccharide composition, hexasaccharide and comparative experimental samples on the latency in the darkness avoidance test in mice with vascular dementia caused by bilateral common carotid artery occlusion. The samples corresponding to the numbers on the abscissa in the Figure are: i: control group; ii: model group; iii: product A; iv: product B; v: product C; vi: product D; vii: comparative experimental sample; viii: hexasaccharide.
Figure 5:
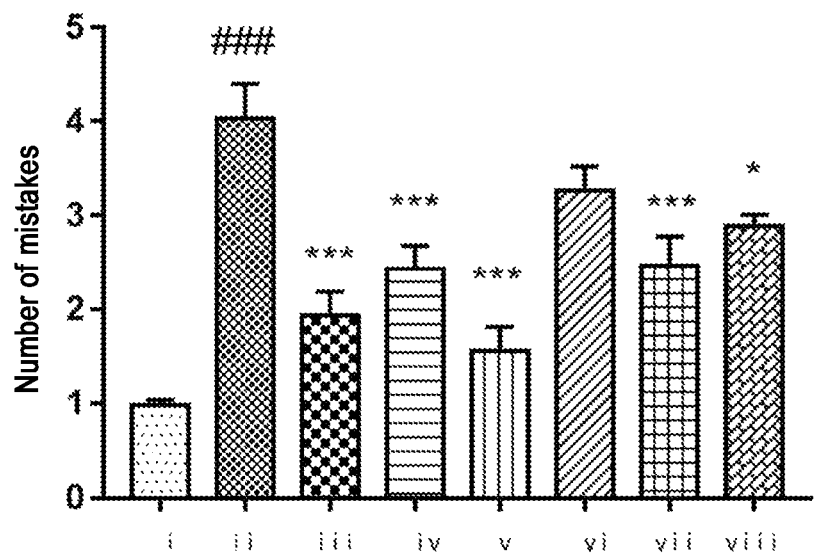
FIG. 5 shows the effects of oligosaccharide composition, hexasaccharide and comparative experimental samples on the number of mistakes in the darkness avoidance test in mice with vascular dementia caused by bilateral common carotid artery occlusion; wherein the symbols on the abscissa are the same as those in FIG. 4.

In the experiment, the model group was compared with the sham operation control group. For the model group, the latency in the darkness avoidance test was significantly shorter, and the number of errors was significantly increased, indicating that the memory ability of the mice in the model group was significantly reduced, and the evaluation model was successfully established. Compared with the model group, the latency in the darkness avoidance test in each dosing group was significantly increased, and the number of errors was significantly reduced. See FIGS. 4 and 5.

1.2 Morris Water Maze Test Results

Figure 6:
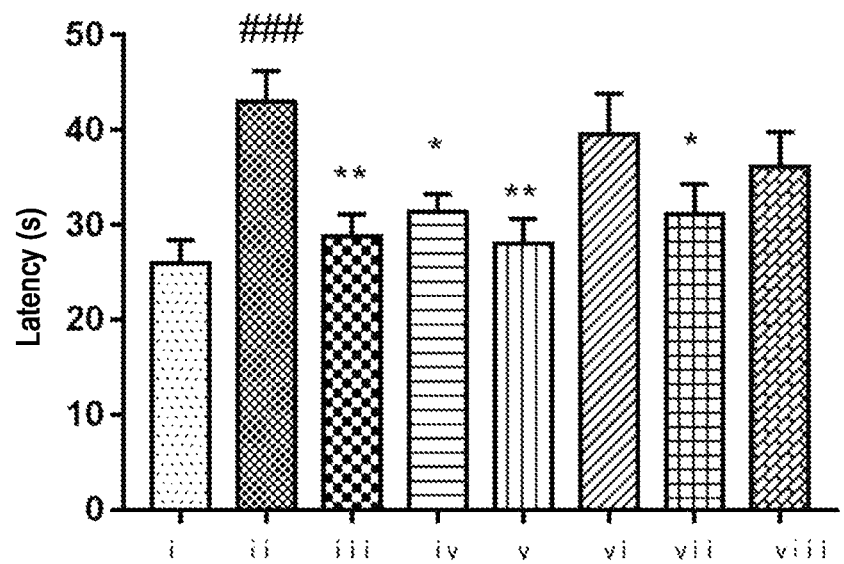
FIG. 6 shows the effects of oligosaccharide composition, hexasaccharide and comparative experimental samples on the escape latency in the water maze test in mice with vascular dementia caused by bilateral common carotid artery occlusion; wherein the symbols on the abscissa are the same as those in FIG. 4.

In the experiment, compared with the sham operation group, the escape latency in the Morris water maze test of the mice in the model group was significantly longer, indicating that the BCCAo-induced mouse vascular dementia model was successfully established. Compared with the model group, the escape latency of each dosing group was significantly shorter. See FIG. 6.

Figure 7:
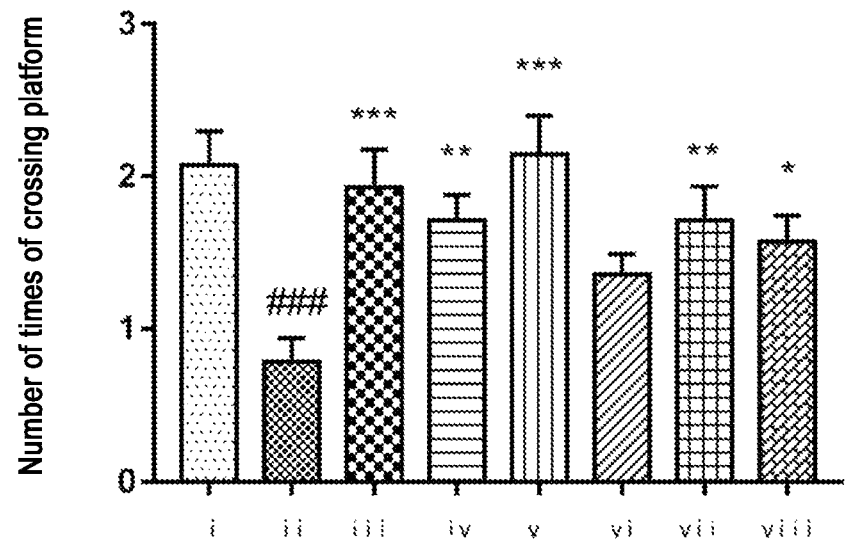
FIG. 7 shows the effects of oligosaccharide composition, hexasaccharide and comparative experimental samples on the number of times of crossing platform in mice with vascular dementia caused by bilateral common carotid artery occlusion; wherein the symbols on the abscissa are the same as those in FIG. 4.

Four days after the water maze place navigation test, the platform was removed for spatial probe test to observe the number of times the animals crossed the platform. Compared with the sham operation group, the number of times that the mice crossed the original platform in the model group was significantly reduced, indicating that the memory ability of the BCCAo mice was significantly reduced; while the number of times the mice crossed the original platform in each dosing group was increased. See FIG. 7.

2. The Effect in the Rats with Vascular Dementia Caused by Middle Cerebral Artery Occlusion (MCAO)

In the experiment, compared with the sham operation group, the escape latency in the Morris water maze test of the rats in the model group was significantly longer, indicating that the MCAO-induced mouse vascular dementia model was successfully established. Compared with the model group, the escape latency of each dosing group was significantly shorter.

Figure 8:
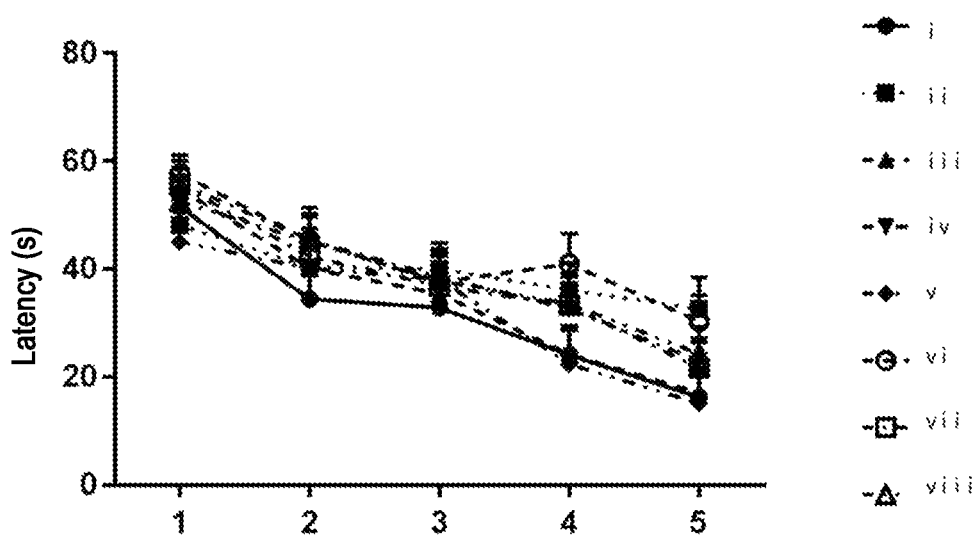
FIG. 8 shows the effects of oligosaccharide composition, hexasaccharide and comparative experimental samples on the escape latency in the water maze test in rats with vascular dementia caused by middle cerebral artery occlusion; wherein the symbols on the abscissa are the same as those in FIG. 4.

A spatial probe test was performed at an interval of 1 day after the place navigation test was finished, to observe and determine the number of times the animal crossed the platform within 2 minutes. Compared with the sham operation group, the number of times the rats crossed the original platform was significantly reduced in the model group, indicating that the memory ability of the rats in the MCAO group was significantly reduced; while the number of times the rats crossed the original platform in each dosing group was increased. See FIG. 8.

The experimental results showed that the pharmacodynamic activity of products A, B and C are all better than the comparative experimental samples, and are better than the previously expected most active hexasaccharide with single polymerization degree. However, the activity of product D is weaker than hexasaccharide. Without being bound by any theory, it is speculated that the proportion of oligosaccharides in the composition has a significant effect on the activity of the product, and adding a certain proportion of disaccharide and trisaccharide has synergistic effect. However, when the proportion of disaccharide and trisaccharide is too high, the activity of the composition would be reduced.

The invention claimed is:

1. A method of treating a patient suffering from vascular dementia; comprising administering to the patient an effective amount of a mannuronic diacid saccharide composition, wherein the mannuronic diacid saccharide composition comprises mannuronic diacids having Formula (III) or a pharmaceutically acceptable salt thereof:

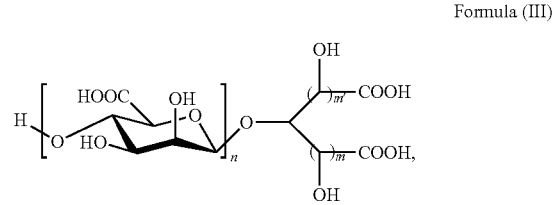

Formula (III)

wherein n is an integer selected from 1 to 9, m is selected from 0, 1 or 2, m' is selected from 0 or 1, and wherein, the total weight of mannuronic diacids wherein n=1-5 accounts for no less than 60% of the total weight of the composition;

the total weight of mannuronic diacids wherein n=1-2 accounts for less than 60% of the total weight of the composition; and wherein in the mannuronic diacid saccharide composition, the total weight of mannuronic diacids with m+m'=1 and 2 is no less than 50% of the total weight of the composition.

2. The method of claim 1, wherein in the mannuronic diacid saccharide composition, the total weight of mannuronic diacids wherein n=1-2 accounts for 10-50% of the total weight of the composition.

3. The method of claim 1, wherein in the mannuronic diacid saccharide composition, the ratio of the total weight of mannuronic diacids wherein n=1-3 to the total weight of mannuronic diacids wherein n=4-7 is between 1.0 and 3.5.

4. The method of claim 1, wherein in the mannuronic diacid saccharide composition, the total weight of mannuronic diacids with m+m'=1 and 2 is 60%-90% of the total weight of the composition.

5. The method of claim 4, wherein the total weight of mannuronic diacids with m+m'=1 is no less than 10% of the total weight of the composition.

6. The method of claim 4, wherein the total weight of mannuronic diacids with m+m'=2 is no less than 10% of the total weight of the composition.

7. The method of claim 1, wherein the total weight of mannuronic diacids wherein n=1-5 accounts for 80-95% of the total weight of the composition.

8. The method of claim 1, wherein the total weight of mannuronic diacids wherein n=1-3 accounts for 20-70% of the total weight of the composition.

9. The method of claim 4, wherein the ratio of the total weight of mannuronic diacids wherein n=1-3 to the total weight of mannuronic diacids wherein n=4-7 is between 1.0 and 3.0.

10. The method of claim 1, wherein the weight percentage content of mannuronic diacids with each of polymerization degrees in the composition is: n=1: 5-25%, n=2: 15-30%, n=3: 15-28%, n=4: 5-25%, n=5: 2-20%, n=6: 2-20%, n=7: 2-20%, n=8: 1-20%, n=9: 1-20%.

11. The method of claim 10, wherein the weight percentage content of mannuronic diacids with each of polymerization degrees in the composition is: n=1: 5-25%, n=2: 15-30%, n=3: 15-28%, n=4: 10-20%, n=5: 5-15%, n=6: 3-10%, n=7: 2-5%, n=8: 1-5%, n=9: 1-5%.

12. The method of claim 11, wherein the weight percentage content of mannuronic diacids with each of polymerization degrees in the composition is: n=1: 10-20%, n=2: 18-30%, n=3: 15-28%, n=4: 15-20%, n=5: 5-10%, n=6: 3-5%, n=7: 2-5%, n=8: 1-3%, n=9: 1-3%.

13. The method of claim 1, wherein the pharmaceutically acceptable salt is sodium salt or potassium salt.

14. The method of claim 1, wherein in the mannuronic diacid saccharide composition, the total weight of mannuronic diacids wherein n=1-2 accounts for 25-50% of the total weight of the composition.

15. The method of claim 1, wherein in the mannuronic diacid saccharide composition, the total weight of mannuronic diacids with m+m'=1 and 2 is 70%-90% of the total weight of the composition.

16. The method of claim 15, wherein the total weight of mannuronic diacids with m+m'=1 is 30-40% of the total weight of the composition.

17. The method of claim 15, wherein the total weight of mannuronic diacids with m+m'=2 is 30-50% of the total weight of the composition.

18. The method of claim 12, wherein the pharmaceutically acceptable salt is sodium salt or potassium salt.

* * * * *